(12) United States Patent
Shkarlet et al.

(10) Patent No.: US 7,469,598 B2
(45) Date of Patent: *Dec. 30, 2008

(54) METHOD OF EMPLOYING A TRANSIT TIME ULTRASOUND SENSOR

(75) Inventors: Yuri Shkarlet, Ithaca, NY (US); Cornelis J. Drost, Ithaca, NY (US)

(73) Assignee: Transonic Systems, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/691,222

(22) Filed: Mar. 26, 2007

(65) Prior Publication Data

US 2007/0186681 A1  Aug. 16, 2007

Related U.S. Application Data

(63) Continuation of application No. 10/447,927, filed on May 29, 2003, now Pat. No. 7,194,919.

(51) Int. Cl.
*G01F 1/20* (2006.01)
*G01D 21/00* (2006.01)
*A61B 8/06* (2006.01)

(52) U.S. Cl. ............... 73/861.18; 73/866.5; 600/459

(58) Field of Classification Search ............ 73/19.1, 73/19.03, 861.27, 861.28, 861.29, 861.31, 73/861.26, 861.25, 861.18, 861.08, 861.05, 73/866.5, 861; 600/459

See application file for complete search history.

(56) References Cited

U.S. PATENT DOCUMENTS 3,674,945 A    7/1972 Hands (Continued)

FOREIGN PATENT DOCUMENTS

DE    3421176 A1    12/1985

(Continued)

OTHER PUBLICATIONS

Drost, C.J., Vessel Diameter-Independent Volume Flow Measurements Using Ultrasound. Proceedings of San Diego Biomedical Symposium, San Diego, CA: San Diego Biomedical Society, vol. 17, p. 299-302, 1978, Transonic Reference; 3T http://www.transonic.com/Research_Home/Research_Support/Technical_Notes/Transit_Time_Theory/body_transit_time_theory.html [online-retrieved on Nov. 11, 1999].

(Continued)

*Primary Examiner*—Hezron Williams
*Assistant Examiner*—Rose M Miller
(74) *Attorney, Agent, or Firm*—Brian B. Shaw, Esq.; Dominic P. Ciminello, Esq.; Harter Secrest & Emery LLP

(57) ABSTRACT

A method is provided for employing a transit time ultrasound sensor, wherein the sensor can be used for the measurement of liquid flow in a conduit, the sensor having an acoustic path formed of materials matched in ultrasound properties to a flow under test, and designed to conform to the shape of the conduit. The transit time ultrasound sensor can be configured as a clamp on device, wherein the conduit walls are constructed from such an ultrasonically-matched material. Alternately, the transit time ultrasound sensor can be employed in a perivascular configuration, wherein the ultrasonically-matched material is operably intermediate the blood vessel and the sensor.

15 Claims, 5 Drawing Sheets

U.S. PATENT DOCUMENTS

| | | | |
|---|---|---|---|
| 4,227,407 A | | 10/1980 | Drost |
| 4,467,659 A | * | 8/1984 | Baumoel .................. 73/861.27 |
| 4,475,054 A | * | 10/1984 | Baumoel .................... 310/335 |
| 4,977,780 A | | 12/1990 | Machida et al. |
| 5,078,148 A | | 1/1992 | Nassi et al. |
| 5,394,732 A | * | 3/1995 | Johnson et al. .............. 73/19.1 |
| 5,440,936 A | | 8/1995 | Spani et al. |
| 5,453,576 A | | 9/1995 | Krivitski |
| 5,462,906 A | * | 10/1995 | Jakubowycz ................. 502/232 |
| 5,463,906 A | | 11/1995 | Spani et al. |
| 5,785,657 A | | 7/1998 | Breyer |
| 5,846,205 A | | 12/1998 | Curley et al. |
| 5,876,345 A | | 3/1999 | Eaton et al. |
| 5,967,989 A | | 10/1999 | Cimochowski et al. |
| 6,098,466 A | | 8/2000 | Shkarlet |
| 6,302,848 B1 | | 10/2001 | Larson et al. |
| 6,537,223 B1 | * | 3/2003 | Kristiansen ................ 600/459 |

FOREIGN PATENT DOCUMENTS

| | | |
|---|---|---|
| EP | 0 128 708 A1 | 12/1984 |
| JP | 62276456 A | 12/1987 |

OTHER PUBLICATIONS

Mannell, Robert, Basic Acoustics, Course notes, 2003, www.ling.mq.edu.au/units/sph301/basic_acoustics/basic_acoustics.html [online-retrieved May 15, 2003].

Elf Atochem, "Pebax, Antistatic Additive, The Key to Permanent Static Dissipative Alloys", online advertisement, http://www.atofinachemicals.com/literature/pdf/25.pdf [online-retrieved at least or early as May 29, 2003].

Omnexus: TPU Ether based ShA - Thermoplastic Urethane Ether based ShA http://www.omnexus.com/tc/polymer_profile.aspx?id=307&tab=3 (2 pages).

The New Omnexus: ABS - Acrylontrile-Butadiene Styrene http://www.omnexus.com/tc/polymerselector/polymerprofiles.aspx (3 pages).

* cited by examiner

METHOD OF EMPLOYING A TRANSIT TIME ULTRASOUND SENSOR

CROSS REFERENCE TO RELATED APPLICATIONS

The present application is a Continuation of U.S. application Ser. No. 10/447,927 filed May 29, 2003 entitled Acoustically Coupled Ultrasonic Transit Time Flow Sensors, which is expressly incorporated by reference.

FIELD OF THE INVENTION

The present invention relates to the use of transit time flow sensors for measuring dynamic parameters of liquid flow in a conduit. More particularly, the present invention relates to an ultrasonic transit time flow sensor having an acoustic path passing through the fluid flow, a conduit, and a solid acoustic couplant, wherein the acoustic parameters of the materials in the acoustic path are matched to provide material interfaces which yield a substantially homogenous full field illumination of the conduit and fluid flow, such that the transit time ultrasound sensor can be employed to measure dynamic parameters of blood flow, such as volume flow rate, cardiac output, and changes in liquid composition.

BACKGROUND OF THE INVENTION

Ultrasonic flow sensors have been employed for a number of years for performing intraoperative or extracorporeal blood flow measurements. Intraoperative flow measurements are typically conducted to monitor dynamic parameters of blood flow in various vessels during vascular, cardiac, transplant, plastic and reconstructive surgery. Flow sensors used for measurements through blood vessels are commonly referred to as perivascular probes. Extracorporeal blood flow measurements are made externally of the patient during procedures in which the blood is removed from the patient for treatment, such as for example, ECMO, hemodialysis, CP bypass and CAVH procedures. Flow sensors used for these purposes on tubing are commonly referred as clamp-on sensors.

While existing ultrasonic blood flowmeters may appear as well suited to perivascular use, this is often not in fact the case. A particular difficulty arises in connection with the coupling of an ultrasound transducer with a vascular vessel. Ultrasound/tissue coupling conventionally involves a water bath, which is often impractical, or a water-soluble gel, which is inappropriate in a wet surgical field.

Prior designs of flow sensors have also included clamping configurations for deforming the conduit wall into a predetermined cross-section of a measuring channel. It is often unacceptable to substantially deform a conduit inside the measuring channel, e.g. in case of blood flow measurements on a human vessel that may be calcified. The squaring could dislodge parts of the calcified plaque which would then become lodged in the microvasculature of the patient and could cause an infarct. If a biocompatible extracorporeal blood line tubing is "squared" inside the flow sensor, the tubing deformation may raise the concern that the sudden change in flow profile could induce thrombosis, or that the deformation itself could damage the inside anti-thrombogenic coating of specialty tubing. Also, the distortion of the conduit alters the average flow and flow profile within the conduit, which constitutes an error in the measurement, in all the situations where the user would want to know the flow through the conduit in its undisturbed state.

Alternatively, the prior flow sensors have included a generally round cross-section for receiving the conduit. However, in these designs, different parts of the ultrasound beam travel different distances through filling member between the transducer to the liquid under the test. The differences in ultrasound velocity between the filling member and the flow under test produce an ultrasound lens, and different parts of the flow will be sensed with different bias in the composite transit-time signal. In addition, a full field flow illumination of the liquid under test is compromised by differences in attenuation between the filling member, the conduit walls and the liquid under test. These differences result in uneven intensity distribution across the flow and thus, to substantially uneven sensitivity distribution inside the measuring channel. All such measurement errors may lead to measurement accuracy specification unacceptable for flow measurements in animal studies and human surgery.

Therefore, the need exists for an ultrasound sensing device and particularly a transit time flow sensor employing planar transmit and receive transducers in an acoustic path, wherein the acoustic path has reduced detrimental interference from passage of an acoustic signal through the conduit or an acoustic coupling. A further need exists for such a transit time flow sensor having a relatively low acoustic attenuation, thereby improving the available signal to noise ratio. The need also exists for a transit time flow sensor that can be employed in non-planar configurations without sacrificing full field illumination or measurement validity.

SUMMARY OF THE INVENTION

The present invention increases the accuracy of ultrasonic transit time flow sensors for measuring dynamic parameters of flowing liquids, such as blood, in a conduit during medical and biomedical investigations including, but not limited to heart or brain surgery and hemodialysis. The transit time flow sensor can monitor or measure parameters including volume flow, cardiac output, as well as any other parameter that can derived from ultrasound time-of-flight measurement (differential and common-mode).

The present invention provides a system that can be employed as a clamp-on (extra-corporeal) sensor or in perivascular measurements of blood flow. The present invention is particularly adapted for transit time ultrasound sensors, and defines a portion of the acoustic path by plastic materials such as a polyether block amide and polyethylene.

In one configuration, the present invention provides a transit time ultrasound flow sensor for measuring a fluid flow in a conduit. The transit time ultrasound flow sensor includes a rigid housing, an upstream transducer and a downstream transducer affixed relative to the housing to define an acoustic path therebetween, and a solid acoustic couplant in the acoustic path to at least partially define a measuring channel, wherein the acoustic path intersects the measuring channel. A conduit is disposed in the measuring channel, wherein the conduit can be a vascular vessel or a synthetic tube, temporarily or permanently located in the measuring channel. The acoustic couplant is a resilient, compliant solid material, which is self-supporting to define at least a portion of the measuring channel. The acoustic couplant allows the measuring channel to be formed to contact a portion of the conduit such that the cross sectional profile of the conduit is substantially free of deformation under contact with the acoustic couplant.

In one configuration, the invention is employed as an extra-corporeal flow-sensing probe, which is selectively clamped onto a conduit of acoustically matched materials, such as polyether block amide. Further, the flow sensing probe may employ planar ultrasound transducers sized to fully illuminate the cross section of the conduit, wherein the conduit is formed of a material having a relatively low temperature coefficient of acoustic velocity; low ultrasound attenuation and matched specific gravity to the flowing liquid. The planar transducers can be oriented in a transmit and receive configuration for transit time through transmission.

In a perivascular configuration, planar emitting and receiving transducers are acoustically coupled to the acoustic couplant forming the measuring channel which is sized to operably receive a section of the vascular vessel. The acoustic couplant can be a material such as a polyether block amide or polyurethane. The acoustic couplant is formulated to acoustically match the blood flow and may be formed in curvilinear cross sectional profiles to accommodate various vessel sizes, without adversely effecting the measurements. That is, the acoustic parameters of the acoustic couplant are selected to preclude detrimental deformation of a wavefront passing through a curvilinear surface of the acoustic couplant. Thus, the present acoustic couplant can form a measuring channel having a curvilinear cross section selected to substantially match that of a vascular vessel or synthetic tube.

Thus, the present invention enhances measurement accuracy by defining an acoustic path between transducers (and reflectors) with a solid self supporting, compliant, resilient acoustic couplant conforming to the conduit wall without detrimentally deforming the conduit wall, conducting ultrasound signals without spatial distortion, attenuation and temperature influence, and having low acoustical losses and matching liquid under the test in acoustical velocity and acoustical impedance.

DETAILED DESCRIPTION OF THE PREFERRED EMBODIMENTS

Figure 1:
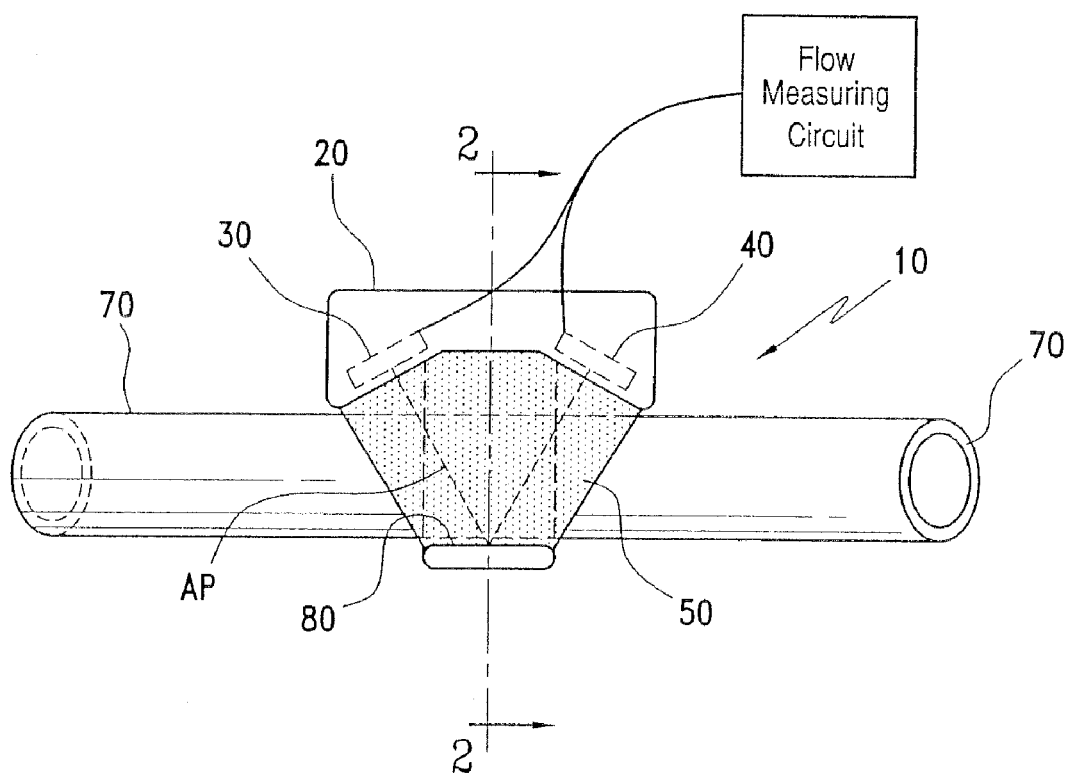
FIG. 1 is a top plan view of a flow sensor for use on arteries, veins or tubing.

Referring to FIGS. 1, 3, 5 and 7, the present invention is an ultrasound transit time flow sensor 10 having a rigid housing or frame 20, an upstream transducer 30 and a downstream transducer 40 affixed relative to the housing to define an acoustic path AP therebetween, and a solid acoustic couplant 50 in the acoustic path, wherein at least a portion of the acoustic couplant defines a portion of a measuring channel 60, such that the acoustic path intersects the measuring channel. The measuring channel 60 is sized to operatively receive a length of the conduit.

A conduit 70 is disposed in the measuring channel 60, wherein the conduit can be a vascular vessel or a synthetic tube. Depending upon the configuration of the flow sensor 10, the conduit 70 can be temporarily or permanently located in the measuring channel 60. The conduit 70 conducts fluid flow through the measuring channel 60.

The housing 20 can include at least one reflector 80 in the acoustic path AP so as to intersect a portion of the acoustic path with the measuring channel 60. It is contemplated that a plurality of reflectors 80 can be used to orient the acoustic path relative to the measuring channel 60. The reflectors 80 are known in the art and are sized to reflect a sufficient area of an acoustic beam to maintain full field illumination.

The flow sensor 10 is generally configured so that an acoustic wavefront (beam) traveling along the acoustic path AP includes at least one of an upstream or a downstream vector with respect to fluid flow in the conduit 70. The inclined intersection of the acoustic path and the fluid flow in the conduit can be provided by a variety of transducer configurations. Specifically, the transducers can cooperate with reflectors to redirect the acoustic path in a variety of configurations such as linear, X or V pattern.

Figure 2:
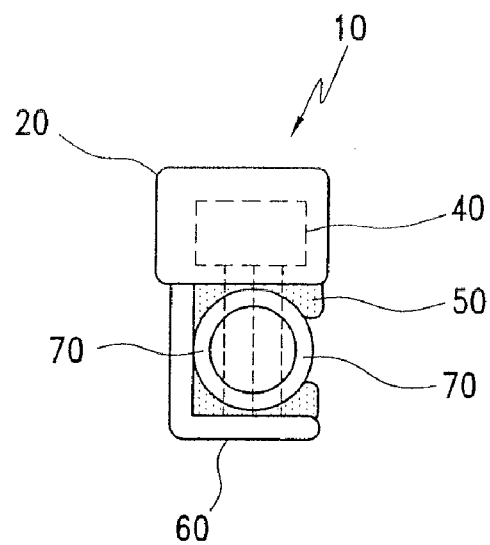
FIG. 2 as a cross sectional view taken along lines 2-2 of FIG. 1.

Specifically, as seen in FIGS. 1 and 2, the acoustic path has a V-shape, wherein the apex of the V is the reflector 80 and the terminal end of each leg is a transducer 30, 40. Thus, as the ultrasound wave travels from the upstream transducer 30 to the reflector 80, the ultrasound wave has a component of travel along the flow path. Similarly, as the ultrasound wave is reflected by the reflector 80 to the downstream transducer 40, the ultrasound wave has a component of travel along the directional flow in the conduit 70. As seen in the figures, the acoustic couplant 50 defines the acoustic path between the respective transducer and the conduit, as well as between the conduit in the reflector. As seen in FIG. 2, the acoustic couplant 50 includes a curvilinear profile for receiving the curvilinear (circular) cross-section of the conduit 70.

Figure 3:
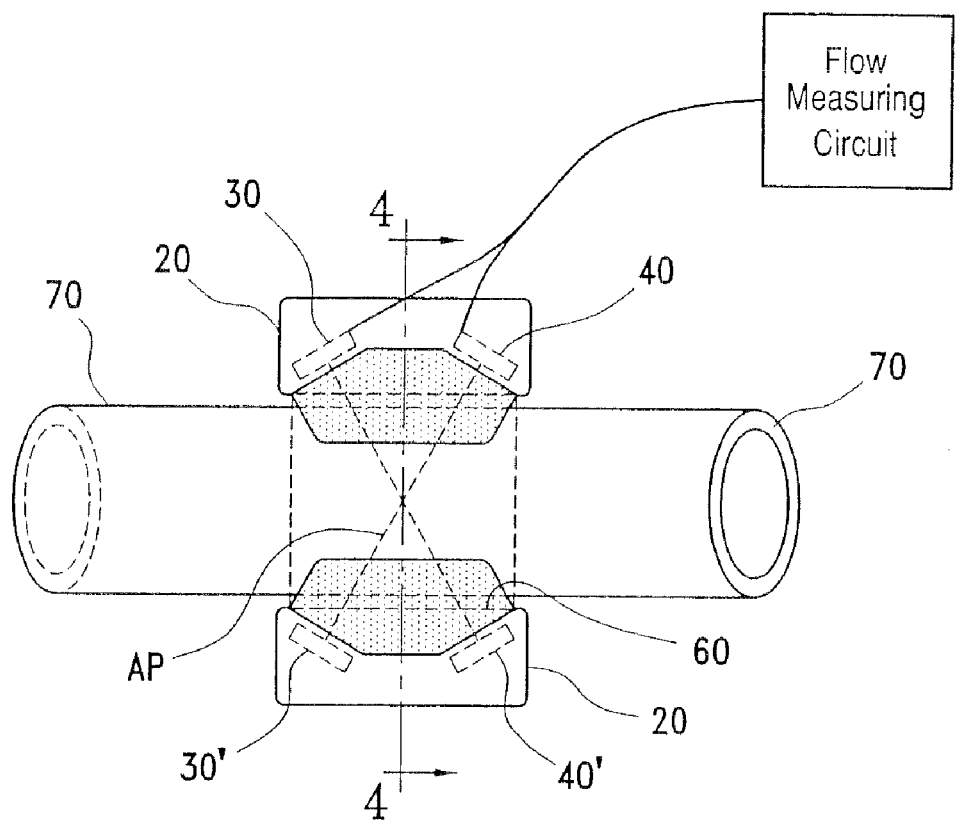
FIG. 3 is a top plan view of a clamp on sensor having a round measuring channel.
Figure 4:
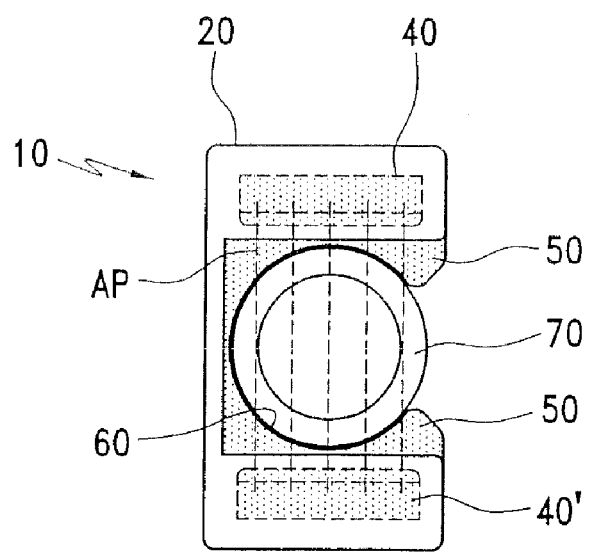
FIG. 4 is a cross sectional view taken along lines 4-4 of FIG. 3.

Referring to FIGS. 3 and 4, the transit time flow sensor 10 can include a plurality of upstream transducers 30, 30' and a plurality of downstream transducers 40,40'. In this configuration, no reflectors are necessary as the downstream transducers 40,40' can be used to record the passage of the signal from the corresponding upstream transducers, and subsequently generate an ultrasound wave in the "upstream" direction. As seen in FIG. 4, the acoustic couplant 50 defines the measuring channel to provide a curvilinear cross section for receiving at least approximately 75% of the periphery of the conduit 70. Preferably, a sufficient portion of the conduit cross-section is disposed within the curvilinear portion of the measuring channel to allow full field illumination by the ultrasound wave. That is, in the full field illumination, the entire cross sectional area of the flow is illuminated.

Figure 5:
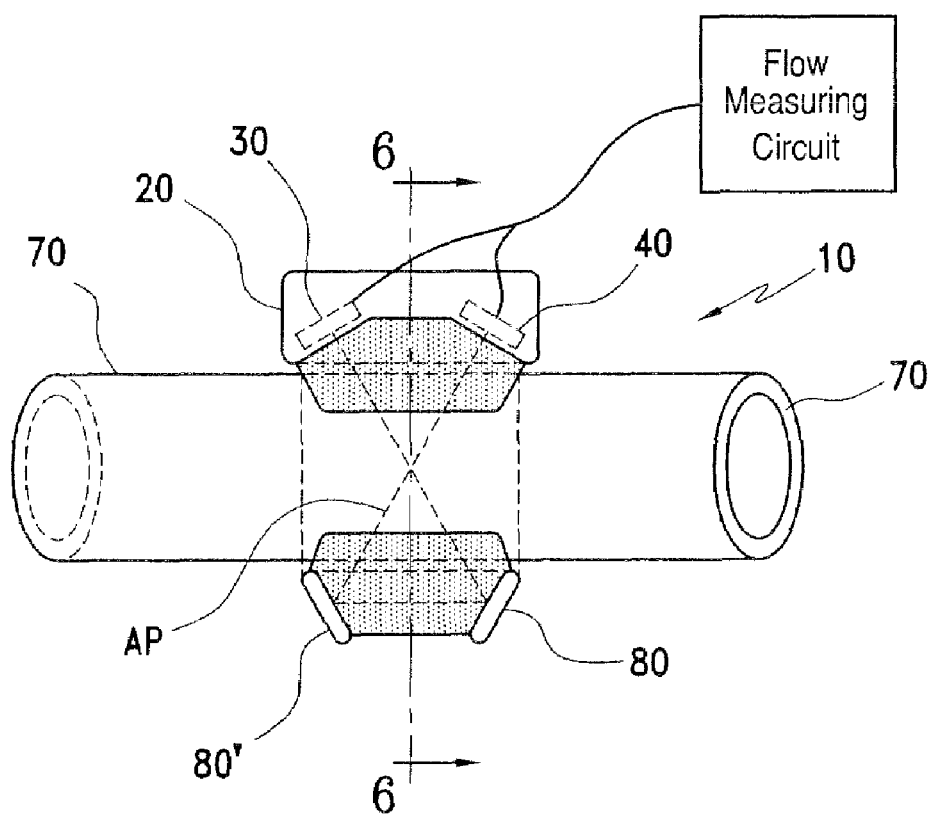
FIG. 5 is a top plan view of a perivascular flow sensing probe.
Figure 6:
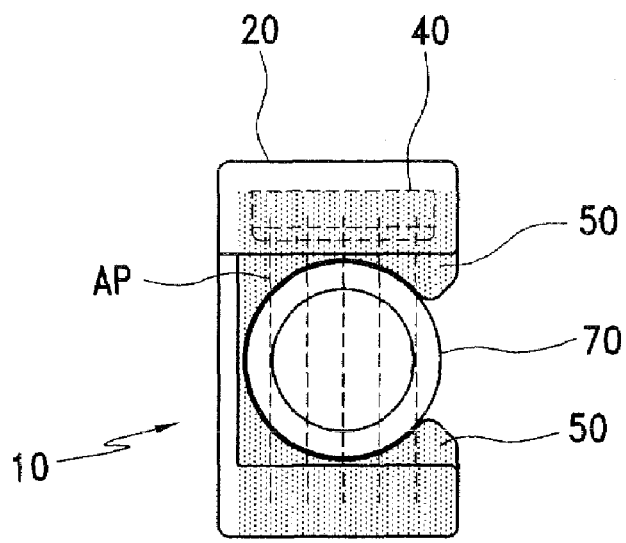
FIG. 6 is a cross sectional view taken along lines 6-6 of FIG. 5.

Referring to FIGS. 5 and 6, the transit time ultrasound flow sensor 10 includes one upstream transducer 30, one downstream transducer 40 and a pair of reflectors 80,80' along the acoustic path intermediate the upstream transducer in the downstream transducer. Referring to FIG. 6, the measuring channel 60 has a curvilinear profile sufficient to retain the corresponding portion of the conduit 70 under full field illumination. The acoustic couplant 50 substantially defines the acoustic path for the upstream transducer 30 to the conduit 70, from the conduit to the downstream reflector 80', from the downstream reflector to the upstream reflector 80, from the upstream reflector 80 to the conduit and from the conduit to the downstream transducer 40. Further, as seen in the figures, the path of the respective ultrasonic wave is substantially linear and is not distorted or reflected by passage across the material interfaces within the acoustic path.

Figure 7:
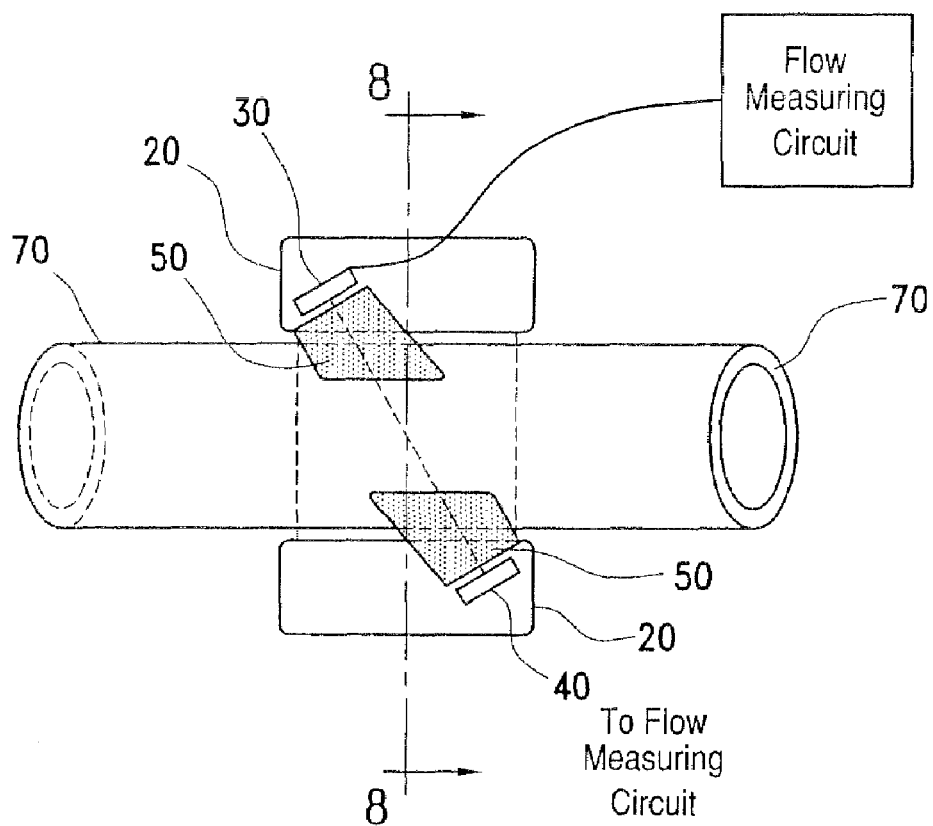
FIG. 7 is a top plan view of an alternative configuration of the flow sensor.
Figure 8:
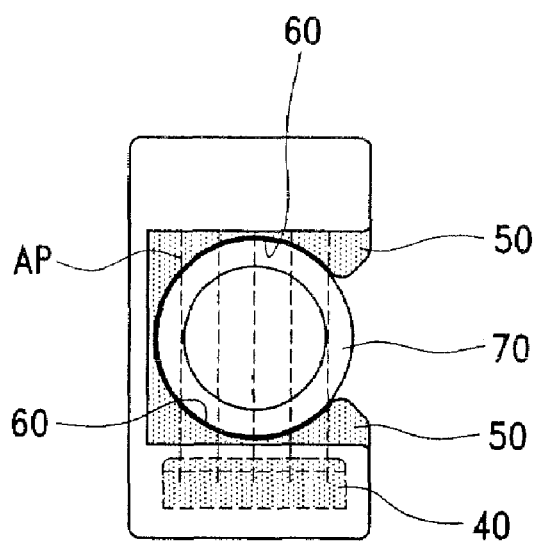
FIG. 8 is a cross sectional view taken along lines 8-8 of FIG. 7.

Referring to FIGS. 7 and 8, the transit time ultrasound flow sensor 10 can include a single upstream transducer 30 and a single downstream transducer 40. The acoustic couplant 50 defines the acoustic path AP from the upstream transducer 30 to the conduit 70 and from the conduit to the downstream transducer 40. Thus, as seen FIGS. 7 and 8, the path of the ultrasonic wavefront is linear and undistorted by passage across the material interfaces in the acoustic path.

Figure 9:
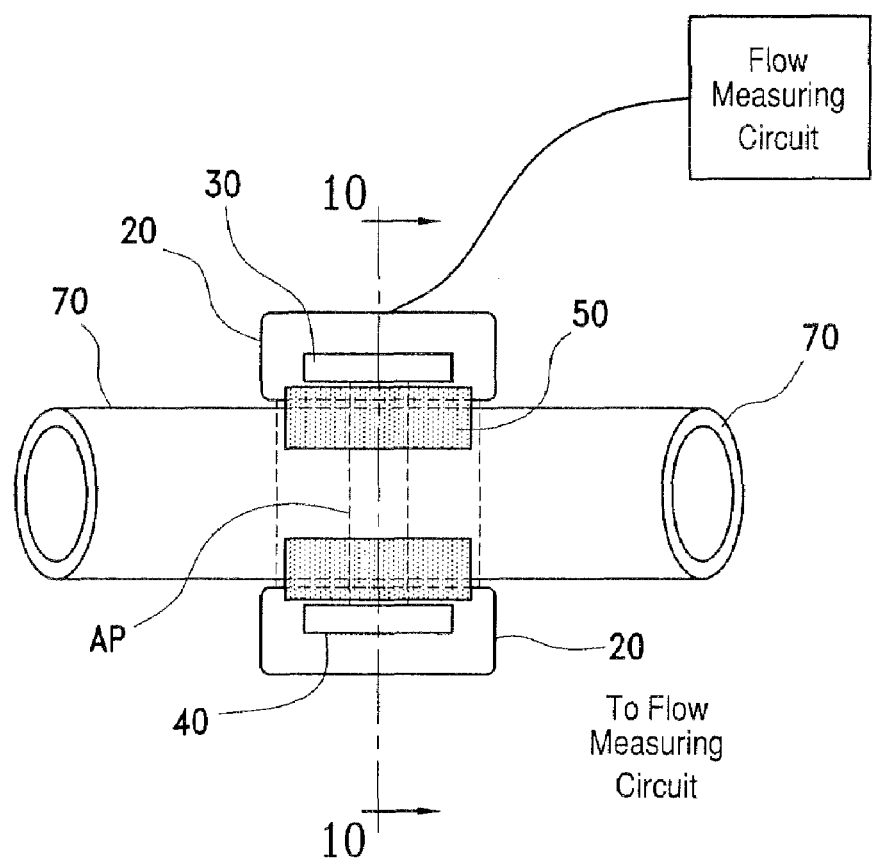
FIG. 9 is a top plan view of an alternative configuration of the flow sensor.
Figure 10:
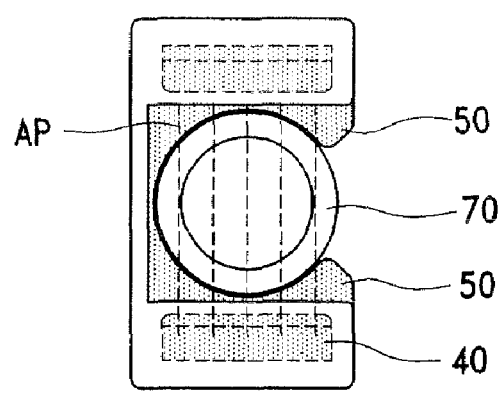
FIG. 10 is a cross sectional view taken along lines 10-10 of FIG. 9.

As seen in FIGS. 9 and 10, the transit time ultrasound flow sensor 10 can include a first transducer 30 and one of a reflector and a second transducer 40 spaced from the first transducer to define the acoustic path AP between the first transducer 30 and the one of the reflector and the second transducer 40. The acoustic couplant 50 defines the acoustic path AP from the first transducer 30 to the conduit 70 and from the conduit to the reflector or second transducer 40. In this configuration it is contemplated the conduit has a curvilinear cross section such as circular, and the acoustic couplant 50 defines a corresponding curvilinear interface with the conduit. Thus, as seen FIGS. 9 and 10, the path of the ultrasonic wavefront is linear and undistorted by passage across the material interfaces in the acoustic path.

The acoustic couplant 50 can define the entire acoustic path from the respective transducer 30, 40 to the conduit 70. That is, the acoustic couplant is integral with a surface of the transducer and forms a continuous solid, yet compliant body to the measuring channel 60. Alternatively, the transducer(s) can be affixed to the housing 20 and a separate material can overlie the surface of the transducer, and the acoustic couplant extend from the separate material to the conduit 70. Thus, the acoustic couplant can define as much as 100% of the acoustic path AP between the transducer 30 (40) and the conduit 70. However, it is understood the acoustic couplant can define as little as 15 to 20% of the acoustic path length.

In the transit-time ultrasound flow sensor 10, a passage time of an ultrasound signal between two transducers is measured. These measurements are used to get differential or common-mode transit time as follows:

Differential Transit Time: the flow of liquid shortens the ultrasound transit time in downstream direction, and lengthens the transit time in upstream direction. The difference between alternate measurements of upstream and downstream transit times can thus be used as a measure of flow rate through the conduit (Cornelis Drost, U.S. Pat. No. 4,227,407, hereby incorporated by reference).

Common-mode transit time: the average value of a downstream and upstream transit time is not a function of flow rate through a conduit, but is a measure of the acoustical velocity of all the media between transmitting and receiving transducers. By introducing a change in this liquid's acoustical velocity (e.g. via the introduction of a bolus of a different liquid, or a momentary change in temperature) it can thus be used as an indicator dilution sensor (see, for example, the methods disclosed in U.S. Pat. Nos. 5,453,576 and 5,595,182, herein incorporated by reference).

All such sensors can measure flow parameters in conduits by employing ultrasound transit-time principles of operation with full flow illumination, wherein the flow cross-section is practically fully and homogeneously illuminated by an ultrasonic beam (Cornelis Drost, U.S. Pat. No. 4,227,407; Shkarlet Yuri, U.S. Pat. No. 6,098,466 incorporated herein by reference).

In the sensor configuration depicted in FIGS. 1-8, the transducer(s) pass ultrasonic signals back and forth, alternately intersecting flowing blood in an upstream and a downstream directions. The transit time of the ultrasonic beam is decreased when traveling downstream with the blood flow and increased when traveling upstream against the flow. The difference between the integrated transit times is a measure of volume flow.

In the sensor configuration depicted in FIGS. 9-10, ultrasound traverses the vessel perpendicularly to the flow and a differential transit time measurement need not be derived. This sensor cannot sense axial flow in the vessel, only common mode transit time, and one need not sequentially reverse the transmit and receive function of the transducers, but may operate the sensor with a single transducer acting as transmitter and receiver by radiating its signal onto a reflector.

During measurements, the conduit with flow under test is inserted into the ultrasonic transit time flow sensor. As the measuring channel 60 can be formed of a round cross section having a curvilinear interface with the conduit, the present flow sensor can be readily used in perivascular or clamp-on environments.

As seen in the drawings, the ultrasonic beam (wave) that passes between the ultrasound transducers intersects a multi-layer (multi-interface) structure that can include the acoustic couplant, the conduit and/or vessel walls, and the liquid under the test.

The transit time sensor 10 is constructed to enhance the accuracy of flow measurements and particularly when the operating conditions, such as liquid temperature, environmental temperature and liquid composition, vary over a range. It has been found that transit time sensor 10 sensitivity is most stable when the acoustic pathway varies the least.

High measurement accuracy requires that the full cross sectional area of flow under test is illuminated with a homogenous uniform level of ultrasound. The full field illumination with uniform level of ultrasound allows all portions of the flow to contribute equally to the transit-time measurement signal, thereby providing an unbiased measure of flow. This is generally achieved through the use of wide ultrasound transducers designed to transmit a constant intensity plane wave of ultrasound, and positioned such that this plane wave of ultrasound illuminates the full cross sectional area of the flow under test with a homogenous level of ultrasound. It is therefore desirable that the even intensity distribution and planar orientation of the ultrasound wave front does not practically (detrimentally) change when the wave front travels across the material interfaces between transducers through the multi-layer structure interposed between flow and the transducers. The design of the flow sensor 10 is selected to avoid material properties and geometries of the multi-layer structure which would distort the even intensity and planar orientation of the ultrasonic field, as such distortions would decrease measurement accuracy.

For example, in the prior art, the spaces between the surfaces of transducers and conduit wall or between a sound-conductive member and a conduit wall are often filled with a gel or liquid having acoustical properties close to those of the flow under the test. However, these liquid and/or gels are not stable, can dry out during a test procedure and may include air bubbles. Air bubbles reflect the ultrasonic beam and distort the planar orientation of wave fronts thus resulting in measurement errors. Multiple reflecting surfaces can introduce errors in measurements.

Thus, the present invention provides filling the acoustic path between the conduit 70 and the transducers 30,40 with the solid acoustic couplant 50. For example, if a sensor 10 includes a plurality of reflectors 80,80' (FIGS. 5 and 6), all the space between the reflectors is filled with the acoustic couplant 50, wherein the acoustic couplant also defines a portion of the measuring channel 60 conforming to the shape of the conduit.

Preferably, the angle of incident of the acoustic beam is equal to the angle of refraction across each interface. That is, the acoustic couplant 50, the conduit 70 and the flow under test all have approximately the same acoustic velocity. Preferably, the acoustic velocity of the acoustic couplant 50, the conduit 70 and the flow under test are within 10%, and more preferably within 5% of each other. This matching of acoustic velocity substantially stabilizes the angle of ultrasound intersecting the fluid flow, when the temperature or liquid properties may vary over a small range.

Examples of such acoustic couplant 50 include, but are not limited to, polyurethane Castall U-2940 from Lord Corporation, polyether block amide (PEBAX from Elf Autochem) and Tecoflex polyurethanes by Thermedics Polymer Products. These materials are produced in different grades, providing a range of acoustical properties to choose from. As an example, the formulation of PEBAX may be selected to match the acoustic velocity of the liquid under test to within 3%, over a range of acoustic velocities of approximately 1480 to 2200 meters per second. If blood is the liquid under the test in the conduit, Pebax 2533 (Shore A hardness 75) or 3533 (Shore A hardness 83) can be used as the acoustic sound-conducting path within the sensor and/or as the conduit. The Pebax 3533 acoustical velocity (about 1,580 m/sec @36° C.) and specific gravity (1.01 g/cm$^3$) provide a near perfect acoustical match with blood. Similarly, Tecoflex 80A and 85A provide a good acoustical velocity match with blood. The specific gravity of such acoustic couplants is substantially equal to that of water, blood, and most water-based chemical solutions, at approximately 1.01. Thus, the acoustic couplant 50 in the present acoustic path AP is selected to match an acoustic velocity of the liquid to within 5% and more preferably within 3%. The acoustic couplant 50 thus provides a resilient, compliant solid that defines the measuring channel 60 having a curvilinear cross section without detrimentally distorting the ultrasound wave front. The acoustic couplant 50 is preferably a solid in contrast to prior gels. The solid acoustic couplant 50 does not flow under shear, and is so firmly adhering, as to resist the impression or penetration of other bodies; and defines a fixed form; as opposed to a fluid, plastic or gel.

The material of the acoustic couplant 50 may equally be used as the conduit or tubing for an extracorporeal circuit, to effect the passage of ultrasound without excessive (or detrimental) wave distortion upon passage through the material, or an interface partially defined by the material. In contrast, prior tubing as used in biomedical applications includes PVC having a Shore A hardness of 75 and an acoustic velocity 1750 meters per second. Thus, the prior tubing has an acoustic velocity that varies from the acoustic velocity of the blood by more than 10%. In contrast, the tubing 70 in the present acoustic path is selected to match an acoustic velocity of the liquid to within 5% and more preferably within 3% to provide passage of the ultrasound measuring signal without detrimentally distorting the ultrasound wave front.

In addition, as stated, the specific gravity of the acoustic couplant 50 is preferably selected to be substantially equal to that of water, blood, and most water-based chemical solutions, at approximately 1.01 grams/cm$^3$. In addition, the specific gravity of the material forming the conduit 70 is selected to be as close as possible to the specific gravity of the liquid flow. By matching the acoustic velocity and specific gravity of the conduit 70 and the liquid, ultrasound signal reflection of these boundaries (interface) is minimized. The lack of signal reflection at these interfaces also increases the signal to noise ratio.

A further complication arises with changes in temperature of the sensor as the attenuation of ultrasound within many plastics varies greatly with temperature. Therefore, in probe designs such as depicted in FIGS. 1-8, where different rays of the ultrasound beam have different path lengths through the acoustic couplant, the constant intensity full flow illumination principle would be further violated by changes in temperature. The same deterioration in measurement accuracy results from tubing materials such as PVC, frequently used inside clamp-on sensors, wherein the ultrasound attenuation is highly temperature-sensitive, and the attenuation of most plastics used for tubing is highly variable even within one grade of plastic. All such variations lead to flow sensitivity distribution change and thus to measurement errors.

The material of the conduit 70 and acoustic couplant 50 are selected to reduce the variation of acoustic velocity with respect to temperature. Preferably, these materials are selected to exhibit a change of approximately two meter per second decrease or less in acoustic velocity for every ° C. increase in temperature. In contrast, the PVC tubing of the prior art has a decrease in acoustic velocity of approximately 8 to 12 meters per second for every ° C. increase.

The material of the tubing 70 and the acoustic couplant 50 are selected with relatively low ultrasound attenuation. Thus, the signal to noise ratio is improved. In the 5 MHz range, the material is selected to provide an attenuation of approximately 1 dB per centimeter. In contrast, the attenuation of prior PVC tubing is on the order of 4-6 dB per cm.

The acoustic couplant 50 is specifically directed towards transit-time flow ultrasonic sensors, where the shape of the measuring channel 60 is designed to match the conduit 70 (FIGS. 1-8). In these flow sensor configurations, ultrasound beam distortion at the sensor-conduit interface is minimized by constructing the acoustic path of the soft-plastic materials with matched acoustical properties. When the conduit 70 is a biological (vascular) vessel, the measuring channel 60 is formed with the acoustic couplant 50 having acoustical parameters close to those of blood and biological tissue (FIGS. 1, 2, 5 and 6). Preferably, the acoustical parameters at the acoustic couplant 50 are within 10% of both the blood and in the biological tissue. In addition, as the measuring channel 60 is formed of a solid acoustic couplant 50 which defines a measuring channel having curvilinear profile, the vascular vessel is not deformed upon operable insertion into the measuring channel. The lack of deformation enhances the integrity of the ultrasound wave and thus increases the accuracy of the sensor.

Thus, for perivascular use, the acoustic couplant 50 will define the measuring channel 60 to have an exposed face concavely profiled to impart a curvilinear, circular, cylindrical shape to compliment the shape of a vascular vessel. Also, because the diametric size of vessels varies, over a range of less than 1 mm to about 36 mm, multiple sensors 10 are configured to have different size measuring channels 60. That is, a first sensor can be constructed with a curvilinear cross section measuring channel 60 to operably receive vessels having a diameter between approximately 1 mm to 2 mm, and a separate second sensor can be constructed with a curvilinear cross section measuring channel sized to operably receive vessels have a diameter between approximately 2 mm to 4 mm. Thus, a plurality of the sensors 10 can be constructed to accommodate the entire spectrum of vessel sizes. In addition, the range of vessel sizes for a given sensor can be as closely matched as desired.

As another embodiment of the present invention, the conduit 70 may be plastic tubing having ultrasound properties similar (matched) to the liquid flowing within the tubing and matched to the sound-conductive members within the acoustic path of the sensor. A tubing wall made of, for instance, Pebax can be easily stretched or deformed to allow insertion into the measuring channel of the style depicted in FIGS. 1-10. Thus, the conduit 70 can be temporarily or permanently affixed to the measuring channel 60.

In summary, there are a number of design requirements to achieve high measurement accuracy in transit time flow sensor design. The present design provides:

The shape of the conduit is optimally maintained at its natural circular (curvilinear) geometry.

Significant differences in acoustical velocity and acoustical impedance at the interfaces of the multi-layer structure within the acoustic path are avoided. The differences between the acoustical velocity and acoustic impedance at interfaces along the acoustic path are selected to minimize distorting of the planar orientation of the wave fronts of the ultrasound beam due to reflection and refraction at the interfaces.

Differences in ultrasound attenuation across interfaces in the acoustic path are reduced to avoid uneven flow sensitivity within the conduit.

Materials within the ultrasound pathway are selected for temperature stability of acoustical properties such as attenuation, acoustical impedance and acoustical velocity.

Sensor materials contacting the conduit should be solid, yet compliant, as high rigidity makes it difficult to maintain a good acoustical contact between the sensor and the vessel under test, thus precluding full flow illumination. That is, a nominal portion of the ultrasound wave (beam) is not detrimentally varied by passage through the materials and interfaces in the acoustic path.

The present transit time ultrasound sensor provides full field illumination of the flow by a substantially coherent planar wave, wherein sufficient coherence is maintained along the acoustic path between the transmitter and the receiver, such that all parts of the wave arrive substantially in phase at the receiving transducer (avoid destructive interference). That is, the coherence is sufficient to provide a resulting summation of all portions of the ultrasonic wave that reach the receiving transducer. The degree of coherence of the wave front and hence the resulting summation value are selected in response to the desired accuracy or resolution. Mathematically, the acoustic waves may be described by parallel wave fronts having a given or nominal period. In this description, the acoustic path and the solid acoustic couplant are selected to match with the fluid (as well as the conduit where possible)so that planar acoustic waves that travel the acoustic path maintain a sufficiently parallel orientation of their wave fronts to permit a summing of the full received signal at the receiving transducer. The same summation requirement is applied when flow through the conduit is sensed, not with a burst of ultrasonic waves but with an ultrasonic pulse. One may consider such a pulse as a half-wave of an ultrasonic frequency, and apply a similar phase cohesion analysis.

In a configuration having adequate accuracy for many applications, the solid acoustic couplant is selected such that the planar cohesion of wave fronts reaching the receiving transducer is maintained to within approximately one-quarter period of the acoustic wave. Thus, as the plane wave intersects the receiver successive wave(s) do not cancel (or destructively interfere with) a prior wave. Thus, if the distortion of the wave fronts along the acoustic path is less than one quarter of its nominal period, the sensed wave fronts can be summed by the receiving transducer to a signal that adequately represents the average dynamic parameters of the liquid within the acoustic path.

While preferred embodiments of the invention have been shown and described with particularity, it will be appreciated that various changes in design and formulas and modifications may suggest themselves to one having ordinary skill in the art upon being apprised of the present invention. It is intended to encompass all such changes and modifications as fall within the scope and spirit of the appended claims.

The invention claimed is:

1. A method of employing a transit time ultrasound sensor, the method comprising:
   (a) disposing a solid acoustic couplant within an acoustic path of the transit time ultrasound sensor, the solid acoustic couplant having an acoustic velocity within 10 percent of a fluid flow in a conduit in the acoustic path and an acoustic impedance within 10 percent of the fluid flow and a wall of the conduit.

2. The method as of claim 1, further comprising determining one of a volume flow or a cardiac output corresponding to the fluid flow in the acoustic path of the transit time ultrasound sensor.

3. The method as in claim 1, further comprising passing a substantially homogenous level of ultrasonic energy through the fluid flow in the acoustic path of the transit time ultrasound sensor.

4. The method of claim 1, further comprising illuminating a substantially full field of the fluid flow in the acoustic path of the transit time ultrasound sensor.

5. A method of employing a transit time ultrasound sensor, the method comprising:
   (a) locating a solid acoustic couplant in an acoustic path of the transit time ultrasound sensor; and
   (b) passing an acoustic wave having a nominal period and a planar wave front along the acoustic path, at least a portion of the planar wave front along the acoustic path reaching a second transducer within $\frac{1}{4}$ of the nominal period.

6. The method of claim 5, further comprising determining one of a volume flow or a cardiac output corresponding to a fluid flow in a conduit located in the acoustic path of the transit time ultrasound sensor.

7. The method of claim 5, further comprising passing a substantially homogenous level of ultrasonic energy through a fluid flow in a conduit located in the acoustic path of the transit time ultrasound sensor.

8. The method of claim 5, further comprising illuminating a substantially full field of a fluid flow in a conduit located in the acoustic path of the transit time ultrasound sensor.

9. The method of claim 5, further comprising illuminating a substantially full field of a conduit located in the acoustic path of the transit time ultrasound sensor.

10. A method of employing a transit time ultrasound sensor, the method comprising:
    (a) locating a conduit having a curvilinear cross sectional profile in an acoustic path of a transit time ultrasound sensor; and
    (b) at least partially defining a measuring channel in the acoustic path to match the curvilinear conduit cross-sectional profile with a solid acoustic couplant in the acoustic path.

11. The method of claim 10, further comprising determining one of a volume flow or a cardiac output corresponding to a fluid flow in the conduit in the acoustic path of the transit time ultrasound sensor.

12. The method of claim 10, further comprising passing a substantially homogenous level of ultrasonic energy through a fluid flow in the conduit in the acoustic path of the transit time ultrasound sensor.

13. The method of claim 10, further comprising illuminating a substantially full field of a fluid flow in the conduit in the acoustic path of the transit time ultrasound sensor.

14. The method as in claims 1, or 10, further comprising illuminating a substantially full field of the conduit in the acoustic path of the transit time ultrasound sensor.

15. The method of claims 1, 5 or 10, further comprising employing a planar transducer in the transit time ultrasound sensor.

* * * * *